United States Patent [19]

Murray

[11] 4,428,902

[45] Jan. 31, 1984

[54] COAL ANALYSIS SYSTEM

[76] Inventor: Kenneth M. Murray, 1425 N. Nash St., Arlington, Va. 22209

[21] Appl. No.: 263,049

[22] Filed: May 13, 1981

[51] Int. Cl.$^3$ .................. G21K 4/00; G21C 17/00
[52] U.S. Cl. ............................ 376/156; 376/157; 378/46
[58] Field of Search ............... 376/153, 156, 157, 166; 378/45, 46, 49

[56] References Cited

U.S. PATENT DOCUMENTS

| 3,974,390 | 8/1976 | Morita et al. | 376/156 |
| 4,031,388 | 6/1977 | Morita et al. | 376/157 |
| 4,278,882 | 7/1981 | Clayton et al. | 376/159 |

OTHER PUBLICATIONS

"Nuclear Tables, Part II Nuclear Reactions", (1965) Kunz et al., vol. 1 pp. 407-409, vol. II p. 204.

S1340-0048, Radiochem. Radioanal. Letters, 5/4-5/pp. 217-222 (1970), Kapitza et al.
S0166-0144, Nuc. Inst. Meth. 84 (1970) pp. 141-143, Johansson et al.
IEEE Trans. on Nuc. Sci. (6/67) pp. 990-991, Wycoff.

Primary Examiner—Sal Cangialosi
Attorney, Agent, or Firm—Melvin L. Crane

[57] ABSTRACT

A system and method of rapidly obtaining quantitative information as to the elemental constituents of coal, particularly the oxygen and sulfer content thereof. The system makes use of the photonuclear interaction to produce the desired radioactivity in the coal constituents. The above mentioned interaction is induced by high energy x-rays from a suitable electron accelerator. The induced radioactivity manifests itself by the emission of characteristic gamma rays among other things. These gamma rays are detected by conventional energy sensitive gamma-ray detectors such as germanium or sodium iodide crystals. The resultant signals are sorted and analyzed to provide the desired information.

9 Claims, 2 Drawing Figures

COAL ANALYSIS SYSTEM

BACKGROUND OF THE INVENTION

This invention relates to the analysis of coal for its impurities such as oxygen, sulfur, and others. More specifically, it relates to a system which takes advantage of the photonuclear interaction to make possible the accurate and rapid determination of these impurities in an "on line" situation. It is well known that such information is of great importance to the efficient and clean operation of coal-fired power plants.

Present techniques of obtaining the impurity information are: (1) conventional chemistry, which is quite slow and is not always representative of the coal being burned at any given instant, and (2) neutron-capture-gamma and activation analysis which, although being much faster than chemistry, suffers from difficulties of count rates, shielding, and processing rate.

SUMMARY OF THE INVENTION

High energy x-rays produced by the electron beam of a small electron accelerator such as a LINAC or a Microtron are used to induce radioactivity in the impurities found in coal. The resultant radioactivity is analyzed by a suitable gamma-ray spectrometer to indicate the amount of impurities present.

DETAILED DESCRIPTION

Figure 1:
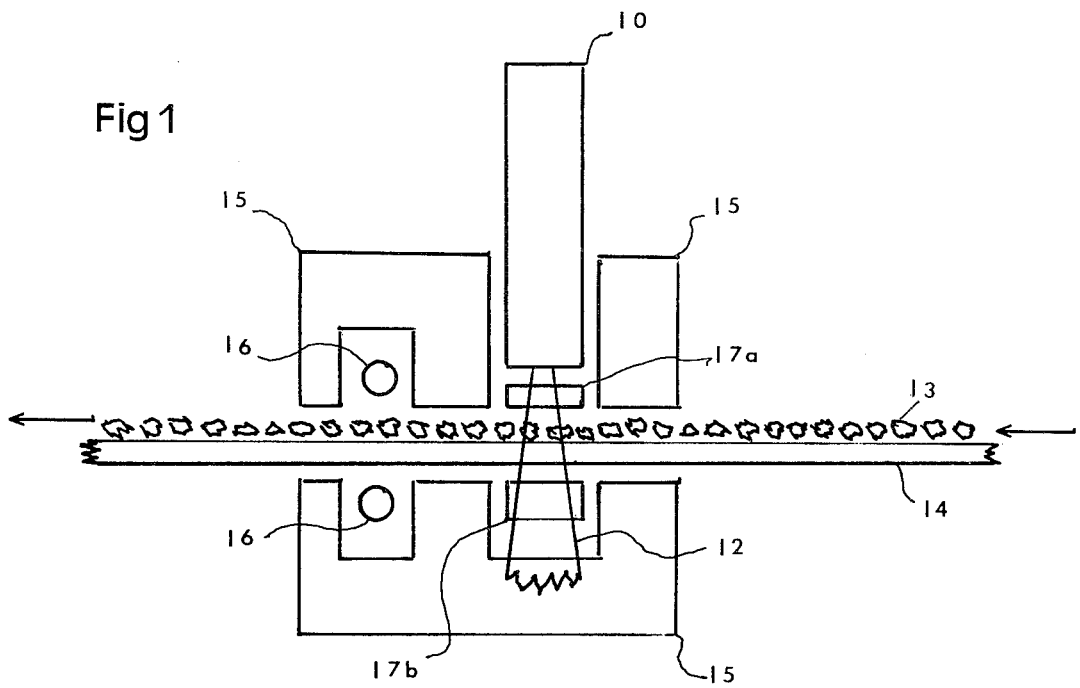
FIG. 1 is a schematic drawing of a preferred coal analysis system according to the invention.

FIG. 1 represents a schematic drawing of a preferred system. A small linear electron accelerator, 10, accelerates a beam of electrons to an energy of 19 Mev and internally converts them to a beam of high energy x-rays, 12. This beam irradiates coal, 13, being carried by a conveyer, 14, passing through the system from right to left as shown in the drawing. The region of irradiation is shielded with thick concrete shields, 15, and the activity induced in the impurities of the coal are detected by crystals, 16, such as germanium or sodium iodide, placed within the shielding, 15, on the "down stream" side of the x-ray beam, 12. The x-ray beam, 12, is measured and absorbed by the monitors, 17a and 17b. Monitor 17a measures the intensity of the x-ray beam before it passes through the coal, while monitor 17b measures the intensity of the beam after it has passed through the coal. The ratio of these two measurements is proportional to the amount of coal being irradiated.

Figure 2:
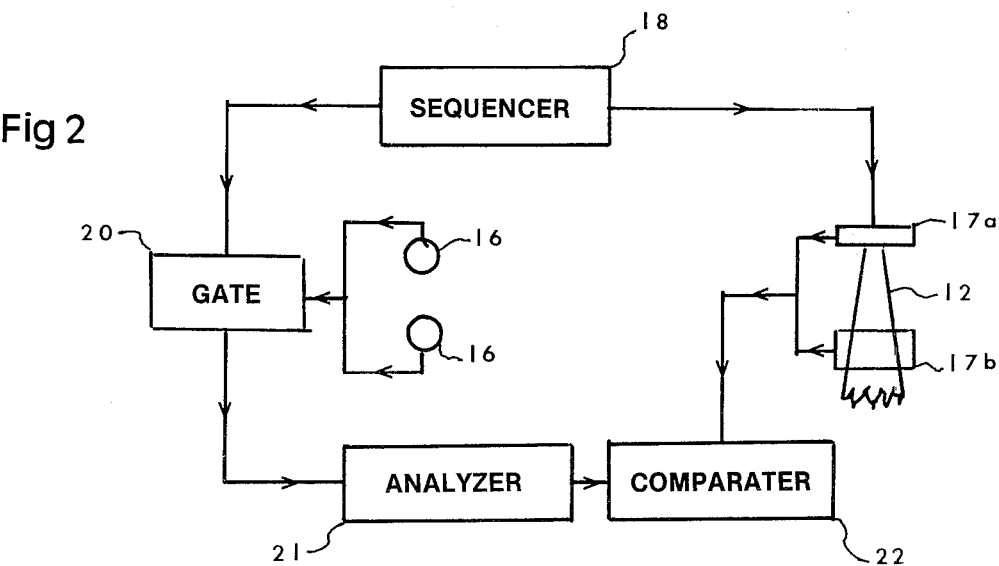
FIG. 2 is a block diagram of a signal processing system suitable for the invention.

The signals of the system are processed by the system indicated in the block diagram shown in FIG. 2. A sequencer, 18, turns on the beam, 12, from the accelerator, for a short period of time, (e.g., 10 seconds). The sequencer, 18, then turns off the beam, 12, long enough for the irradiated coal, 13, to move to a position between the crystals, 16, where the radioactivity is counted. The sequencer, 18, now turns on a gate, 20, allowing the signals from the crystals, 16, to be analyzed by a pulse-height-analyzer, 21. The data in the pulse-height-analyzer, 21, is scanned for peaks in the spectrum of pulse heights obtained from the crystals, 16, by a comparator, 22. This comparator, 22, reads the integral of each peak from the analyzer and divides it by a number derived from the ratio of the measurements made by the beam monitors, 17a and 17b. The quantities thus derived are adjusted at each gamma-ray energy for the efficiency of the detection system at that energy. By this means, the percentages of impurities in the coal is displayed by the comparator, 22, and controlling signals are provided to modify the operation of the power plant as desired. After the irradiated coal, 13, has been analyzed for a short period of time (e.g., 10 seconds), the sequencer, 18, gates off the crystals, 16, and the beam, 12, is turned on to irradiate the next sample of coal, 13. This process is continued so long as there is coal to be analyzed.

The primary advantage of the above described system is that it does not make the carbon in the coal radioactive. This is achieved by limiting the energy of the electron beam to 19 Mev. Since coal is predominantly carbon, this means that only the impurities are made radioactive, thereby virtually eliminating unwanted background. This makes possible quick and accurate determination of oxygen sulfur, and other impurity content of the coal.

A further advantage of this system is that this system can be switched off whenever desired, whereas, a radioactive neutron source cannot.

A further advantage of using an electron accelerator is that the beam travels in a well defined direction, whereas, the neutron source radiates isotropically.

Obviously many modifications of the present invention are possible in light of the above teachings. It is therefore to be understood that within the scope of the appended claims the invention may be practiced otherwise than as specifically described.

What is claimed and desired to be secured by Letters Patent of the United States is:

1. An on line coal analysis coal analysis system for continuously analyzing a moving quantity of coal which comprises;
    an electron accelerating means for providing an electron beam not greater than 19 Mev;
    an electron beam converting means positioned so as to convert the electron beam from the electron accelerating means into an x-ray beam for the purpose of irradiating a portion of said moving quantity of coal;
    at least one x-ray beam monitoring means positioned so as to monitor the x-ray beam from the electron beam converting means subsequent to passage of said x-ray beam through said portion of said moving coal;
    a radioactive detection means downstream of said x-ray monitor a predetermined distance for providing signals characteristic of the detected radioactivity;
    an analyzer means to sort the signals from the radioactivity detection means according to their amplitude.

2. A system as claimed in claim 1 wherein:
    a second x-ray beam monitoring means is placed so as to measure the x-ray beam prior to its passage through said portion of said moving quantity of coal.

3. A system as claimed in claim 1 wherein;
    a comparator means is included which will determine and integrate peaks in the signal amplitude distribution provided by the analyzer means.

4. A system as claimed in claim 3 wherein;

the comparator means will also divide the integral of each peak by a number proportional to a measurement of the x-ray beam made by the x-ray beam monitoring means.

5. A system as claimed in 3 wherein;
the comparator means will also divide the integral of each peak by a number proportional to a ratio of the measurements made by the x-ray beam monitoring means.

6. A system as claimed in claim 3, wherein;
the comparator means will also multiply the integral of each peak by a previoulsy determined efficiency of the radioactivity detection means for the energy of the radioactive emination representing that peak.

7. A system as claimed in claim 4 wherein;
the comparator means will also multiply the integral of each peak by a previously determined efficiency of the radioactivity detection means for the energy of the radioactivity emination represented by that peak.

8. A system as claimed in claim 5 wherein;
the comparator means will also multiply the integral of each peak by a previously determined efficiency of the radioactivity detection means for the energy of the radioactive emination represented by that peak.

9. A method of analyzing a continuously moving quantity of coal which comprises:
producing an electron beam of not greater than 19 Mev by use of an electron accerlerating means;
directing said electron beam onto an electron beam converting means so as to convert the electron beam into an x-ray beam for the purpose of irradiating a portion of said moving quantity of coal;
monitoring said x-ray beam produced by said electron beam converting means subsequent to passage of said x-ray beam through said portion of said moving coal by use of x-ray beam monitoring means;
positioning a radioactive detection means downstream of said x-ray beam monitoring means to detect any radioactivity and to provide signals characteristic of the detected radioactivity; and
analyzing the detected radioactivity signals by use of an analyzer means to sort the signals from the radioactivity detection means according to their amplitude.

* * * * *